United States Patent
Von Waldkirch

(10) Patent No.: US 10,416,140 B2
(45) Date of Patent: Sep. 17, 2019

(54) GAS SENSOR WITH TEMPERATURE CONTROL

(71) Applicant: Sensirion AG, Stafa (CH)

(72) Inventor: Marc Von Waldkirch, Zurich (CH)

(73) Assignee: Sensirion AG, Stafa (CH)

( * ) Notice: Subject to any disclaimer, the term of this patent is extended or adjusted under 35 U.S.C. 154(b) by 219 days.

(21) Appl. No.: 14/161,021

(22) Filed: Jan. 22, 2014

(65) Prior Publication Data

US 2014/0208828 A1    Jul. 31, 2014

(30) Foreign Application Priority Data

Jan. 31, 2013    (EP) .................................. 13405020

(51) Int. Cl.
G01N 27/12    (2006.01)
G01N 33/00    (2006.01)

(52) U.S. Cl.
CPC ....... *G01N 33/0031* (2013.01); *G01N 27/123* (2013.01)

(58) Field of Classification Search
CPC .. G01N 27/12; G01N 27/123; G01N 33/0031; G01N 27/18; G01N 27/20; Y10S 257/93; G01K 7/02; G01K 7/24
(Continued)

(56) References Cited

U.S. PATENT DOCUMENTS 2,861,114 A  * 11/1958 Nishimura ................ C22C 5/04
                                                   136/236.1
5,824,271 A  * 10/1998 Frank ..................... G01N 27/12
                                                   338/34
(Continued)

FOREIGN PATENT DOCUMENTS

GB    2464016    7/2010
WO    9519563    7/1995
WO    0250528    6/2002

OTHER PUBLICATIONS

Non-Patent Literature "Combined Resistive and Calorimetric Sensing of Gases Using a Single Silicon Micromachine Device", Shin, Hyun Woo, Craig Lloyd and Julian W. Gardner, Transducers '97, 1997 International Conferene on Solid-State Sensors and Actuators, Chicago, Jun. 16-19, 1997, pp. 935-938.*

(Continued)

*Primary Examiner* — Jonathan M Dunlap
*Assistant Examiner* — Irving A Campbell
(74) *Attorney, Agent, or Firm* — Cooper & Dunham LLP

(57) ABSTRACT

A gas sensor comprises a metal oxide sensing patch, a heater for heating the sensing patch, electrodes for measuring the conductivity of the sensing patch and an evaluation unit for generating a resulting parameter indicative of at least one analyte. Further, a temperature sensor is provided for measuring the temperature at the location of the sensing patch. The evaluation unit is adapted to derive a first parameter indicative of the conductivity of the sensing patch and a second parameter indicative of the heating power required to maintain a desired temperature of the sensing patch or indicative of the deviation of the temperature at the sensing patch from the desired temperature. The evaluation unit further combines the first and second parameters for evaluating the resulting parameter, thereby using the sensing patch not only as a chemiresistor but also as a pellistor-type measurement device.

16 Claims, 2 Drawing Sheets

(58) Field of Classification Search
USPC .............. 73/23.2, 23.21, 23.31, 25.05, 31.05;
257/347, 414; 338/34; 340/632; 422/83,
422/95, 96, 94; 436/147, 149, 153;
438/49
See application file for complete search history.

(56) References Cited

U.S. PATENT DOCUMENTS

| | | | | |
|---|---|---|---|---|
| 6,111,280 | A * | 8/2000 | Gardner | G01N 27/4141 |
| | | | | 257/253 |
| 6,540,892 | B1 * | 4/2003 | Strohmaier | F02D 41/1494 |
| | | | | 204/408 |
| 2003/0147449 | A1 * | 8/2003 | Chavan | G01J 5/14 |
| | | | | 374/137 |
| 2005/0087024 | A1 | 4/2005 | Steiner et al. | |
| 2008/0128285 | A1 | 6/2008 | Moon et al. | |
| 2009/0215180 | A1 * | 8/2009 | Bos | G01N 27/122 |
| | | | | 436/8 |
| 2013/0085709 | A1 * | 4/2013 | Stark | G01K 3/06 |
| | | | | 702/133 |

OTHER PUBLICATIONS

Non-Patent Literature "A Hybrid Electronic Nose System for Monitoring the Quality of Portable Water", Hyun Woo Shin, doctoral thesis, University of Warwick School of Engineering, Oct. 1999, pp. i-194.*

* cited by examiner

GAS SENSOR WITH TEMPERATURE CONTROL

TECHNICAL FIELD

The invention relates to a gas sensor for measuring at least one analyte in a gas. The gas sensor comprises a patch of sensing material and electrodes in contact with the patch for measuring a parameter indicative of the electrical conductivity of the patch. The patch can be heated by a heater. A temperature sensor is provided for measuring the temperature at the location of the patch.

BACKGROUND ART

A sensor of this type is described in GB 2464016. It uses a patch of metal oxide that changes its electrical conductivity depending on the composition of the gas that it is exposed to. The patch is heated to a suitable operating temperature, typically in the range of 300° C.-600° C. The patch is arranged on a membrane for thermal insulation and thermally coupled to a heater. The heater also acts as a temperature sensor for monitoring the temperature at the location of the patch, and a closed loop temperature control is provided for maintaining an accurate temperature.

The sensor is adapted to detect the presence, in particular the concentration, of an analyte by processing the current flowing through the electrodes.

DISCLOSURE OF THE INVENTION

The problem to be solved by the present invention is to provide a gas sensor and a method that allow a more accurate detection of the analyte.

This problem is solved by the sensor and device according to the independent claims.

Accordingly, the invention relates to a gas sensor for measuring at least one analyte in a gas that comprises the following elements:

A patch of sensing material having an electrical conductivity depending on a concentration of the analyte.

Electrodes in electrical contact with said patch of sensing material. These electrodes can be used to measure the conductivity of the patch.

A heater arranged at a location of said patch. This heater can be used to control the temperature of the patch, e.g. at an elevated operating temperature of at least 100° C., in particular of at least 300° C.

A first temperature sensor for measuring the temperature at the location of said patch. This temperature sensor can be an individual component, but it may e.g. also be incorporated into the heater because the heater's resistance is also indicative of the temperature at the location of the patch. The first temperature sensor may yield a signal that is indicative of an absolute temperature or of a relative temperature.

A temperature controller having a feedback loop controlling a current through said heater in order to try to maintain the temperature at the location of said patch at a desired value.

An evaluation unit adapted to measure a first parameter indicative of the electrical conductivity of the patch.

Said evaluation unit is further adapted to measure a second parameter indicative a) of the heating power required to maintain said temperature at the desired temperature and/or b) of a deviation of the temperature at the location of said patch from said desired temperature.

This second parameter can e.g. be a parameter indicative of the heating current sent by the temperature controller through the heater (case a). Or it can e.g. be a parameter indicative of the difference between the desired temperature and the temperature at the location of the heater (case b).

The evaluation unit is adapted and structured to combine the first parameter and second parameter for evaluating a resulting parameter indicative of a presence of said analyte in said gas. This resulting parameter can e.g. simply indicate if the analyte is present, or it may e.g. be a value indicating the concentration of the analyte. As mentioned, the resulting parameter is evaluated from a combination of the first and the second parameter, i.e. the evaluation unit is adapted to use both these parameters when determining the resulting parameter and the resulting parameter is a function depending on the first and the second parameter.

This technique takes advantage of the fact that typical sensing materials induce an exo- or endothermal decomposition of the analyte, which gives rise to a change of the current required to maintain the desired temperature and/or to a temperature deviation of the temperature at the location of the patch from the desired temperature. Therefore, the patch of sensing material is used for two purposes, namely:

as a chemoresistor that changes its electrical conductivity in the presence of the analyte and as a catalyst in a calorimetric determination of the analyte (catalytic pellistor-type measurement).

Especially advantageous sensing materials that change their conductivity in the presence of numerous analytes and act as catalysts are metal oxides, in particular tin oxide or tungsten oxide.

The second parameter can be derived from the temperature signal from the first temperature sensor, i.e. from the same temperature sensor that is also used for controlling the patch temperature. In another embodiment, though, a second temperature sensor may be provided in addition to the first temperature sensor, and the evaluation unit is adapted to derive the second parameter using the signal from the second temperature sensor. This allows to optimize the second temperature sensor for its specific purpose.

The second parameter can be derived from comparing a measurement with the analyte with a measurement that is or was taken without the analyte. Also, a calibration curve relating the membrane over-temperature to the heating power in the absence of the analyte can be compared to the current heating power and membrane temperature.

Advantageously, the gas sensor may comprise a temperature difference sensor adapted to measure a temperature difference. In particular, this temperature difference sensor can comprise at least one thermocouple. The temperature difference sensor generates a signal indicative of the difference of the temperature at the location of the patch and a temperature elsewhere on the sensor. The evaluation unit is adapted and structured to derive the second parameter from the signal of this temperature difference sensor This is particularly advantageous in order to eliminate environmental effects, such as thermal fluctuations due to environmental temperature changes or airflow at the location of the sensor.

In an advantageous method the heater is made of a first metal and the electrodes are made of a second metal, with the first metal being different from the second metal. In that case, the difference temperature sensor can be made of a thermocouple of said first and second metal.

In a particularly advantageous embodiment, the first metal is tungsten and the second metal is platinum.

The invention also relates to a method for operating a gas sensor of the type above that comprises the following steps:
- Trying to keep the temperature at the location of said patch constant by controlling a current through said heater.
- Determining a first parameter indicative an electrical conductivity of said patch,
- Determining a second parameter indicative
  a) of a heating power required to maintain said temperature at the desired temperature and/or
  b) of a deviation of the temperature at the location of said patch from said desired temperature.
- Combining said first and second parameters for evaluating a resulting parameter indicative of a presence of said analyte in said gas.

Other advantageous embodiments are listed in the dependent claims as well as in the description below.

The invention also relates to a mobile phone or a tablet computer comprising a gas sensor as described above.

BRIEF DESCRIPTION OF THE DRAWINGS

The invention will be better understood and objects other than those set forth above will become apparent from the following detailed description thereof. Such description makes reference to the annexed drawings, wherein.

Note: The figures are not to scale.

MODES FOR CARRYING OUT THE INVENTION

Definitions

Terms indicating a vertical direction or arrangement, such as "top", "bottom", "above" or "below" relate to a frame of reference where the batch of material layers forming the membrane are arranged on top, i.e. above, the substrate. In other words, the substrate is arranged, by definition, below the material layers and the membrane is located on top of the opening extending through the substrate.

The term "lateral" is used to describe directions parallel to the top and bottom surfaces of the semiconductor substrate.

The term "a parameter indicative of" a property is to be understood as a parameter that depends on the mentioned property, advantageously a parameter that is (at least over a subrange of the values of the given property) an invertible function of the given property. For example, a parameter indicative of a temperature can be a value that is proportional to the temperature or to the logarithm of the temperature.

The term "tungsten" as used herein is to be understood as designating pure tungsten as well as any material, in particular an alloy, comprising at least 90%, in particular at least 95%, of tungsten.

The term "platinum" as used herein is to be understood as designating pure platinum as well as any material, in particular an alloy, comprising at least 90%, in particular at least 95%, of platinum.

Figure 1:
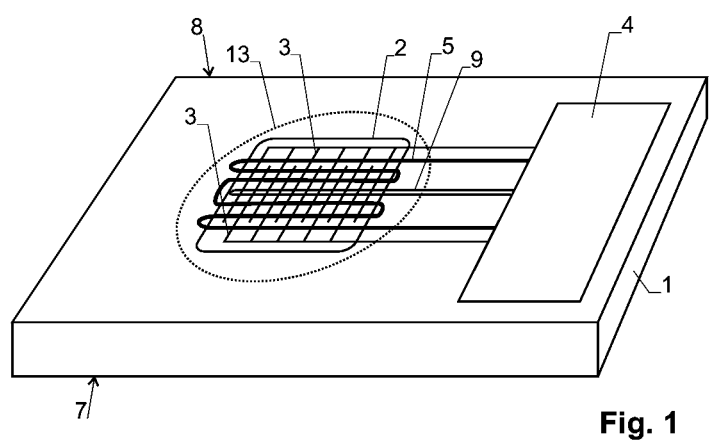
FIG. 1 shows a view of a first embodiment of a gas sensor.

The device:

FIG. 1 shows a gas sensor adapted to generate a signal indicative of the concentration or presence of at least one gaseous analyte in a gaseous carrier, such as alcohol in air. It comprises a semiconductor substrate 1. A sensor material, whose electrical properties depend on the concentration of the analyte, is applied to substrate 1 in a sensing patch 2. For example, sensing patch 2 consists of a granular layer of tin oxide, or of another material whose electrical resistance depends on the presence and concentration of various compounds in the surrounding atmosphere. This type of device is e.g. described in GB 2464016 or in WO 95/19563.

Sensing patch 2 is in electrical contact with at least a pair of interdigitated electrodes 3, advantageously of platinum or gold, which are connected to processing circuitry 4. Processing circuitry 4 is implemented as CMOS circuitry integrated on semiconductor substrate 1 and can e.g. comprise active components, such as transistors, at least one amplifier, at least one analog/digital converter, and/or interface circuitry, etc.

The sensor device further comprises a heater 5, advantageously of tungsten, positioned at the location of sensing patch 2 in order to heat sensing patch 2 to its operating temperature, which, for tin oxide, is e.g. typically at least 300° C.

The device is also equipped with a first temperature sensor 9 for measuring the temperature at the location of sensing patch 2 on membrane 13 (see below). In the shown embodiment, first temperature sensor 9 is a resistive temperature sensor. It is advantageously of the same material as heater 5 or it is of the same material as the electrodes 3, such that no additional electrically conductive layer is required at the location of membrane 13.

Figure 2:
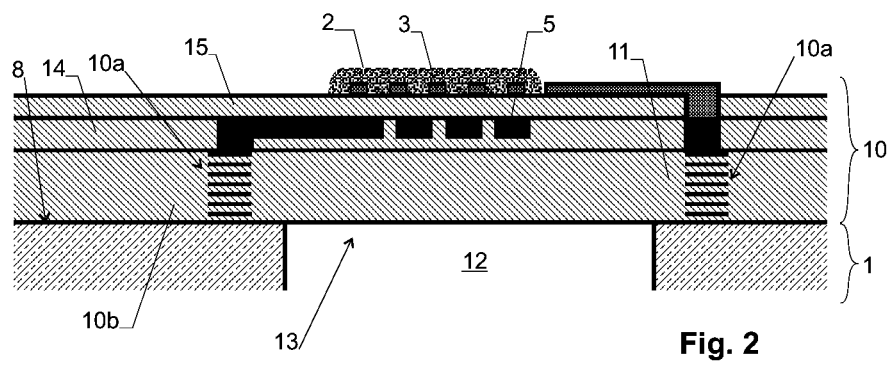
FIG. 2 shows a sectional view of the gas sensor.

FIG. 2 shows a sectional view of this type of device. As can be seen, semiconductor substrate 1 comprises a bottom surface 7 (cf. FIG. 1) and a top surface 8. A batch 10 of material layers is applied to top surface 8 and typically comprises a plurality of structured dielectric layers and a plurality of structured metal layers.

A bottommost part 10a of the various metal layers is typically of aluminum (or AlCu or copper) and forms interconnects of the CMOS circuitry. In FIG. 2, the metal layers 10a are only shown schematically. They are separated by dielectric layers, typically silicon oxide layers, which are generally denoted by reference number 10b.

Parts of the layers of batch 10 extend over an opening 12 or recess in semiconductor substrate 1 and form a membrane 13. Membrane 13 can have circular or rectangular shape or any other suitable shape.

Advantageously, and in order to reduce the thermal conductivity of membrane 13, none of the metal layers 10 extends into membrane 13.

Batch 10 can further comprise a layer of silicon nitride (not shown) under tensile stress, which extends at least over membrane 13 and is anchored laterally outside membrane 13. The tensile stress in this layer can be at least sufficiently large to exceed the compressive stress in the rest membrane 13, which leads to a total tensile stress in the membrane. As described in U.S. Pat. No. 7,154,372, such a tensile layer can be used to prevent the membrane from buckling.

Heater 5 and any other structures formed from the same material layer as heater 5 are formed, e.g. in a Damascene process, by structuring a tungsten layer into metal conductors, which are located in a silicon oxide layer (or other dielectric layer) 14 on membrane 13. As seen in FIG. 1, the metal conductor can e.g. follow a meandering path.

A dielectric layer, e.g. a silicon oxide layer, 15 is arranged on top of the layer of heater 5 and electrically insulates the same from a platinum layer forming the electrodes 3 and first temperature sensor 9.

A protective dielectric layer can be applied to the top of the device (not shown).

Sensing patch 2 is arranged on top of the electrodes 3 and in contact therewith. It can e.g. be applied using printing techniques.

Figure 3:
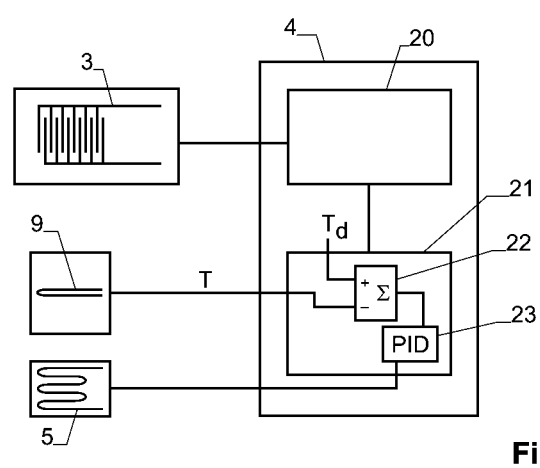
FIG. 3 shows a block diagram of the first embodiment of the gas sensor.

Block diagram, operation:

FIG. 3 shows the block diagram of a first embodiment of a gas sensor. As can be seen, processing circuitry 4 comprises an evaluation unit 20 as well as a temperature controller 21. Evaluation unit 20 and/or temperature controller 21 is/are advantageously integrated as CMOS circuitry on substrate 1.

Temperature controller 21 is connected to first temperature sensor 9 and heater 5. It comprises a closed control loop that tries to keep the temperature T measured by first temperature sensor 9 at a desired temperature $T_d$ by controlling the current through heater 5. Such closed control loops are known to the skilled person and can e.g. comprise a comparator 22 comparing current temperature T to desired temperature $T_d$ and calculating the difference $T_d-T$ and a filter 23, such as a PID filter, for generating a signal indicative of the desired heating power.

Evaluation unit 20 is connected to the electrodes 3 as well as to temperature controller 21. As mentioned above, it is used to determine a "resulting parameter" $p_r$ indicative of the analyte to be measured. This resulting parameter is a function F of at least a first parameter $p_1$ and a second parameter $p_2$, i.e.

$$p_r = F(p_1, p_2) \qquad (1)$$

First parameter $p_1$ is indicative of the electrical conductivity of sensing patch 2, e.g. derived from the current flowing from the electrodes 3 through sensing patch 2 when a voltage is applied thereto, and it can e.g. be a value proportional to the resistance or conductivity of sensing patch 2.

Second parameter $p_2$ can, in a first alternative, be indicative of the heating power required to maintain the desired temperature $T_d$. For example, it can be equal to or be derived from the output of filter 23.

In a second alternative, second parameter $p_2$ can be indicative of a deviation of current temperature T at the location of sensing patch 2 and desired temperature $T_d$. For example, it can be equal to or be derived from the output of comparator 22.

First parameter $p_1$ depends on the conductivity of the sensing material, which is a function of the concentration and type of the analyte.

Second parameter $p_2$ depends on the heat loss at the location of sensing patch 2, which in turn depends of the rate and heat of reaction of the catalytic decomposition of the analyte at the sensing material. Therefore, second parameter $p_2$ also depends on the concentration and type of the analyte, albeit differently from first parameter $p_1$.

Hence, by combining $p_1$ and $p_2$ in a suitable function F as described by Eq. (1), it becomes possible to derive more accurate information on the concentration and/or type of the analyte than it would be possible from parameter $p_1$ or $p_2$ alone.

Function F of Eq. (1) can e.g. be determined from a series of calibration measurements with one or more analytes. Suitable methods to do so are known to the skilled person.

Further Embodiments

Figure 4:
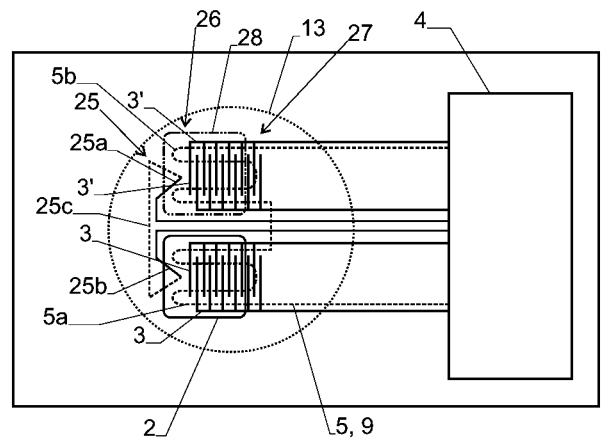
FIG. 4 shows a top view of a second embodiment of a gas sensor.

FIG. 4 shows a top view of a second embodiment of a gas sensor. It illustrates some concepts that differ from those of the first embodiment.

A first such concept is the implementation of first temperature sensor 9. In the embodiment of FIG. 4, temperature sensor 9 is formed by heater 5. Since the resistance of heater 5 is a function of temperature, heater 5 can also be used as a temperature sensor.

A second aspect in which the embodiment of FIG. 4 differs from the one of FIGS. 1-3 is the measurement of second parameter $p_2$. In the embodiment of FIG. 2, a second temperature sensor 25 is provided on the gas sensor in addition to first temperature sensor 9.

Advantageously, second temperature sensor 25 is a temperature difference sensor that measures a difference of the temperature at the location of sensing patch 2 and a temperature elsewhere on the sensor.

For example, second temperature sensor 25 can measure the temperature difference between the location of sensing patch 2 and a location away from membrane 13 over the bulk of substrate 1, which allows to determine the temperature of sensing patch 2 in reference to the environmental temperature.

However, advantageously, the temperature difference sensor is adapted to measure the temperature difference between the location of sensing patch 2 and a second location 26 on membrane 13. The second location is at a distance from sensing patch 2, in particular at a distance of at least 10 µm, in particular of at least 50 µm, in order to have a good thermal insulation between second location 26 and sensing patch 2.

In this case, heater 5 is advantageously arranged to heat not only the location of sensing patch 2 but also second location 26. For example, and as shown in FIG. 4, heater 5 may consist of two parts arranged in series or in parallel, with the first part 5a heating the location of sensing patch 2 and the second part 5b heating second location 26.

Since second location 26 is at a distance from sensing patch 2, the thermal effects of the decomposition of the analyte at the sensing material will have a much stronger influence on the temperature at sensing patch 2 than on the temperature at second location 26. On the other hand, other phenomena giving rise to a temperature change on the sensor, such as a gas flow, gas temperature or gas convection, will have similar effects at the location of sensing patch 2 as well as second location 26. Hence, measuring the temperature difference by means of temperature difference sensor 25 allows evaluation unit 20 to determine a more accurate resulting parameter $p_r$.

Advantageously, a reference structure 27 is arranged at second location 26 on membrane 13. This reference structure has thermal properties that are identical or nearly identical to those of the structure at the location of sensing patch 2. For example, and as shown in FIG. 4, reference structure 27 can comprise reference electrodes 3', which ideally have the same design as those at the location sensing patch 2. Also, heater 5 has, at second location 26, the same design as it has at the location of sensing patch 2. Further, a reference patch 28 can be arranged at second location 26, which reference patch has basically the same shape, heat capacity and heat conductivity as sensing patch 2 but that has different chemical properties. For example, reference patch 28 can be formed by the same material as sensing patch 2 but be coated with a gas-impermeable layer that prevents the analyte from reacting at reference patch 28, or reference patch 28 can be of a more conventional, chemically inert material, such as granular silicon oxide.

In more general terms, reference structure 27 at second location 26 should advantageously have, within an accuracy of 33% or better, in particular 10% or better, the same size (width and length), heat capacity and heat conductivity as the combination of heater 5, electrodes 3 and sensing patch 2 at the location of sensing patch 2. In this case, the temperature difference between the location of sensing patch 2 and second location 26 will primarily depend on the thermal effects of the catalytic decomposition of the analyte at sensing patch 2.

Temperature difference sensor 25 advantageously comprises at least one thermocouple. Advantageously, it is made of the materials of heater 5 and the electrodes 3, if these are different, such that no further conducting layer is required in the region of membrane 13. In the example of FIG. 4, the thermocouple comprises at least one electrical conductor (in the shown embodiment of two conductors 25a and 25b) of the same material as the electrodes 3 and of at least one electrical conductor 25c of the same material as heater 5.

For example, as mentioned above, heater 5 can be of tungsten and the electrodes 3 of platinum, or of gold, in which case the thermocouple comprises at least a first conductor of tungsten and at least a second conductor of gold or platinum.

Instead of using a thermocouple for measuring the temperature difference between the location of sensing patch 2 and the second location 25, two resistive temperature sensors, e.g. of one of the materials of heater 5 or the electrodes 3, can be used as well. In this case, the temperature difference can be derived using two temperature-dependent resistors e.g. arranged in a Wheatstone bridge.

Notes:

In the above example, the heater is of tungsten and the electrodes are of platinum. Other materials may be used as well, e.g. electrodes of gold. Also, in particular for lower temperature, the heater can e.g. also be of polysilicon or aluminium.

The invention claimed is:

1. A gas sensor for measuring at least one analyte in a gas comprising
    a sensing patch of sensing material having an electrical conductivity depending on a concentration of the analyte,
    electrodes in electrical contact with said sensing patch of sensing material,
    a heater arranged at a location of said sensing patch,
    a first temperature sensor for measuring a temperature at the location of said sensing patch,
    a temperature controller having a feedback loop controlling a current through said heater in order to try to maintain said temperature at the location of said sensing patch at a desired value, and
    an evaluation unit adapted to measure a first parameter dependent on an electrical conductivity of said sensing patch,
    characterized in that said evaluation unit is further adapted
        to measure a second parameter dependent on
            a) a heating power required to maintain said temperature at the desired temperature and/or
            b) a deviation of the temperature at the location of said sensing patch from said desired temperature
        and to evaluate a resulting parameter indicative of a presence or concentration of said at least one analyte from a combination of both the first parameter and the second parameter, the resulting parameter being a function depending on both the first parameter and the second parameter, the second parameter being indicative of an exothermal or endothermal decomposition of the analyte, and both the first parameter and the second parameter depending on the concentration and type of analyte,
    wherein said temperature controller and/or said evaluation unit is/are integrated on a substrate carrying said sensing patch,
    said gas sensor further comprising a second temperature sensor, in addition to said first temperature sensor, wherein said evaluation unit is further adapted to derive said second parameter using a signal from said second temperature sensor.

2. The gas sensor of claim 1 further comprising
    the substrate,
    a recess or opening in said substrate,
    a membrane extending over said recess or opening,
    wherein said sensing patch, said electrodes, said heater and said first temperature sensor are arranged on said membrane.

3. The gas sensor of claim 1 wherein said sensing material is a metal oxide.

4. The gas sensor of claim 3 wherein said sensing material is tin oxide or tungsten oxide.

5. A mobile electronic device comprising the gas sensor of claim 1.

6. The mobile electronic device of claim 5, wherein the mobile electronic device is a mobile phone or a tablet computer.

7. A method for operating the gas sensor of claim 1 comprising the steps of
    trying to keep the temperature at the location of said sensing patch constant by controlling the current through said heater,
    determining the first parameter dependent on the electrical conductivity of said sensing patch,
    determining the second parameter dependent on
        a) the heating power required to maintain said temperature at the desired temperature and/or
        b) the deviation of the temperature at the location of said sensing patch from said desired temperature, and
    evaluating the resulting parameter indicative of the presence or concentration of said at least one analyte from the combination of both the first parameter and the second parameter, the resulting parameter being the function depending on both the first parameter and the second parameter, the second parameter being indicative of an exothermal or endothermal decomposition of the analyte, and both the first parameter and the second parameter depending on the concentration and type of analyte.

8. A gas sensor for measuring at least one analyte in a gas comprising
    a sensing patch of sensing material having an electrical conductivity depending on a concentration of the analyte,
    electrodes in electrical contact with said sensing patch of sensing material,
    a heater arranged at a location of said sensing patch,
    a first temperature sensor for measuring a temperature at the location of said sensing patch,
    a temperature controller having a feedback loop controlling a current through said heater in order to try to maintain said temperature at the location of said sensing patch at a desired value, and an evaluation unit adapted to measure a first parameter dependent on an electrical conductivity of said sensing patch, characterized in that said evaluation unit is further adapted to measure a second parameter dependent on
- a) a heating power required to maintain said temperature at the desired temperature and/or
- b) a deviation of the temperature at the location of said sensing patch from said desired temperature and to evaluate a resulting parameter indicative of a presence or concentration of said at least one analyte from a combination of both the first parameter and the second parameter, the resulting parameter being a function depending on both the first parameter and the second parameter, the second parameter being indicative of an exothermal or endothermal decomposition of the analyte, and both the first parameter and the second parameter depending on the concentration and type of analyte, wherein said temperature controller and/or said evaluation unit is/are integrated on a substrate carrying said sensing patch, said gas sensor further comprising a temperature difference sensor for measuring a difference of the temperature at the location of the sensing patch and a temperature elsewhere on the gas sensor, wherein said evaluation unit is adapted to determine said second parameter from a signal of said temperature difference sensor.

9. The gas sensor of claim 8, wherein said temperature difference sensor is adapted to measure said temperature difference between the location of the sensing patch and a second location on said membrane, wherein said second location is at a distance from said sensing patch.

10. The gas sensor of claim 9 wherein said heater is arranged to heat the location of said sensing patch and said second location.

11. The gas sensor of claim 9 further comprising a reference structure at said second location, wherein said reference structure has, within an accuracy of 33%, a same width and length, heat capacity and heat conductivity as a combination of said heater, said electrodes and said sensing patch at the location of the sensing patch.

12. The gas sensor of claim 11, wherein said reference structure has, within an accuracy of 10%, a same width and length, heat capacity and heat conductivity as a combination of said heater, said electrodes and said sensing patch at the location of the sensing patch.

13. The gas sensor of claim 8 wherein said heater is of a first material and said electrodes are of a second material different from said first material and wherein said temperature difference sensor comprises at least one thermocouple of said first and said second materials.

14. The gas sensor of claim 13 wherein said first material is tungsten and said second material is platinum or gold.

15. The gas sensor of claim 8 wherein said temperature difference sensor comprises two temperature-dependent resistors arranged in a Wheatstone bridge.

16. The gas sensor of claim 8 wherein said temperature difference sensor comprises two temperature-dependent resistors arranged in a Wheatstone bridge and wherein said heater is made of tungsten and said electrodes are made of platinum or gold.

* * * * *